(12) United States Patent
Yamazaki et al.

(10) Patent No.: US 7,008,350 B1
(45) Date of Patent: Mar. 7, 2006

(54) HEALTH AMOUNT-OF-EXERCISE MANAGING DEVICE

(75) Inventors: Iwao Yamazaki, Tokyo (JP); Kimiyo Yamazaki, Tokyo (JP)

(73) Assignee: Ya-Man Ltd., Tokyo (JP)

( * ) Notice: Subject to any disclaimer, the term of this patent is extended or adjusted under 35 U.S.C. 154(b) by 0 days.

(21) Appl. No.: 10/030,168

(22) PCT Filed: Dec. 9, 1999

(86) PCT No.: PCT/JP99/06913

§ 371 (c)(1),
(2), (4) Date: Jan. 31, 2002

(87) PCT Pub. No.: WO01/15601

PCT Pub. Date: Mar. 8, 2001

(30) Foreign Application Priority Data

Aug. 30, 1999 (JP) .................................. 11-243421

(51) Int. Cl.
    A63B 21/00 (2006.01)
    A63B 5/05 (2006.01)

(52) U.S. Cl. .............................. 482/8; 482/9; 600/300; 600/547

(58) Field of Classification Search ................ 482/1–9, 482/900–902; 600/300, 547
    See application file for complete search history.

(56) References Cited

U.S. PATENT DOCUMENTS 5,372,141 A * 12/1994 Gallup et al. ................ 600/547
5,410,471 A * 4/1995 Alyfuku et al. ............. 600/300
5,817,031 A * 10/1998 Masuo et al. ................ 600/547
6,354,996 B1 * 3/2002 Drinan et al. ............... 600/300

* cited by examiner

Primary Examiner—Glenn E. Richman
(74) Attorney, Agent, or Firm—Bacon & Thomas

(57) ABSTRACT

To permit a person to take a power-striding most effective to be healthy the quantity of exercising is managed by using, in combination, bioelectrical impedance measuring means 110; personal data inputting means 120; body fat rate calculating means 130 for determining the body fat rate on the basis of the personal data and the value of bioelectrical impedance; target body fat rate setting means 140; target calorie consumption calculator means 150 for calculating the calorie consumption required to attain the target body fat rate; management period setting means 160 for setting a length of period required to attain the target body fat rate; healthful calorie consumption calculator means 170 for calculating the calorie consumption per day within the management period; walking calorie per minute calculating means 180 for calculating caloric quantity consumed by walking per minute in consideration of the individual basal metastasis; healthful exercise quantity calculating means 190 for calculating the healthful exercise quantity per day required to consume the healthful calorie per day; exercise quantity measuring means 200; calorie consumption per day calculating means 210 for determining the calorie consumption on the basis of the so measured exercise quantity; and healthful exercise quantity correcting means 220 for comparing the calorie consumption per day of the previous day with the target value of the present day and for converting any difference therebetween in terms of exercise quantity, thereby renewing the healthful exercise quantity of the present day.

4 Claims, 4 Drawing Sheets

HEALTH AMOUNT-OF-EXERCISE MANAGING DEVICE

TECHNICAL FIELD

The present invention relates to an apparatus for managing the quantity of exercising to be healthy, using a body fat meter along with a pedometer or an accelerometer for measuring vertical shaky movement.

BACKGROUND ART

In order that the fatness may be reduced continuously toward the ideal body fat rate (17–24% for women, and 14–20% for men) it is necessary that not only weight but also body fat rate be measured almost everyday, thereby realizing the condition of fatness; an adequate quantity of exercise be determined on the basis of the degree of fatness; and the so determined quantity of exercising to be fat less and less be continued for a long time without an off day.

In general, the energy required to move muscles is produced both from saccharine and fat. Excessively hard exercise consumes saccharine rather than fat, and therefore, such excessively hard exercise has the effect of improving the cardiorespinatory functional capacity (endurance capacity), but little or no effect of reducing fatness.

In order to burn the fat for the purpose of reducing the degree of fatness it is necessary that an appropriate exercise be selected and taken at an appropriate degree of hardness. From this point of view the power-striding is most recommendable.

In order to exercise to be healthy it is difficult to determine how much and long the power-striding should be taken and continued.

What is aimed at by the present invention is that: means for determining the quantity of exercise and a body fat meter are so combined that the condition of fatness may be realized everyday, and the quantity of exercise to be taken each day may be determined on the basis of the degree of fatness, thus permitting one to exercise to be healthy with an increased efficiency.

SUMMARY OF THE INVENTION

An apparatus for managing the quantity of exercising to be healthy, comprises:
 a portable casing with a display fixed thereon, the casing having exercise quantity measuring means installed therein;
 at least one set of electrodes fixed to the surface of said portable casing for measuring bioelectrical impedance;
 data inputting means for inputting personal data including sex, age, height and weight; and
 body fat rate calculating means for determining the body fat rate on the basis of the personal data and the value of bioelectrical impedance, which bio-electrical impedance appears between two selected electrodes when a controlled weak current flows between the two selected electrodes through a living body,
whereby the exercise quantity along with the body fat rate are shown in said display.

An apparatus for managing the quantity of exercising to be healthy, further comprises:
 basal metastasis estimating means for estimating the basal metastasis on the basis of said personal data and said body fat rate;
 exercise quantity estimating means for estimating the total exercise quantity on the basis of data provided from said exercise quantity measuring means;
 calorie consumption calculating means for determining the calorie consumption on the basis of the estimated basal metastasis and the total exercise quantity;
 caloric intake inputting means for inputting the calorie taken in by drinking and taking food; and
 caloric balance calculating-and-displaying means for determining the difference between the caloric intake per day and the calorie consumption and for displaying the balance between the caloric intake and the calorie consumption.

An apparatus for managing the quantity of exercising to be healthy, comprises:
 a portable casing with a display fixed thereon, the casing having exercise quantity measuring means installed therein;
 at least one set of electrodes fixed to the surface of said portable casing for measuring bioelectrical impedance;
 data inputting means for inputting personal data including sex, age, height and weight;
 body fat rate calculating means for determining the body fat rate on the basis of the personal data and the value of bioelectrical impedance, which bioelectrical impedance appears between two selected electrodes when a controlled weak current flows between the two selected electrodes through a living body;
 body fat rate setting means for setting a desired body fat rate as a target; and
 healthful exercising quantity setting means for determining the quantity of exercising each day toward the desired body fat rate on the basis of the so determined body fat rate and for setting the so determined quantity of exercise per day, whereby the exercise quantity along with the body fat rate and the healthful exercising quantity per day are shown in said display.

An apparatus for managing the quantity of exercising to be healthy as defined in claim 4, in addition to all the means of claim 3, further comprises healthful exercising quantity renewing means for renewing the healthful exercising quantity per day in consideration of the exercising quantity determined the day before, the required renewal being made every day.

DETAILED DESCRIPTION OF THE PREFERRED EMBODIMENT

Figure 1:
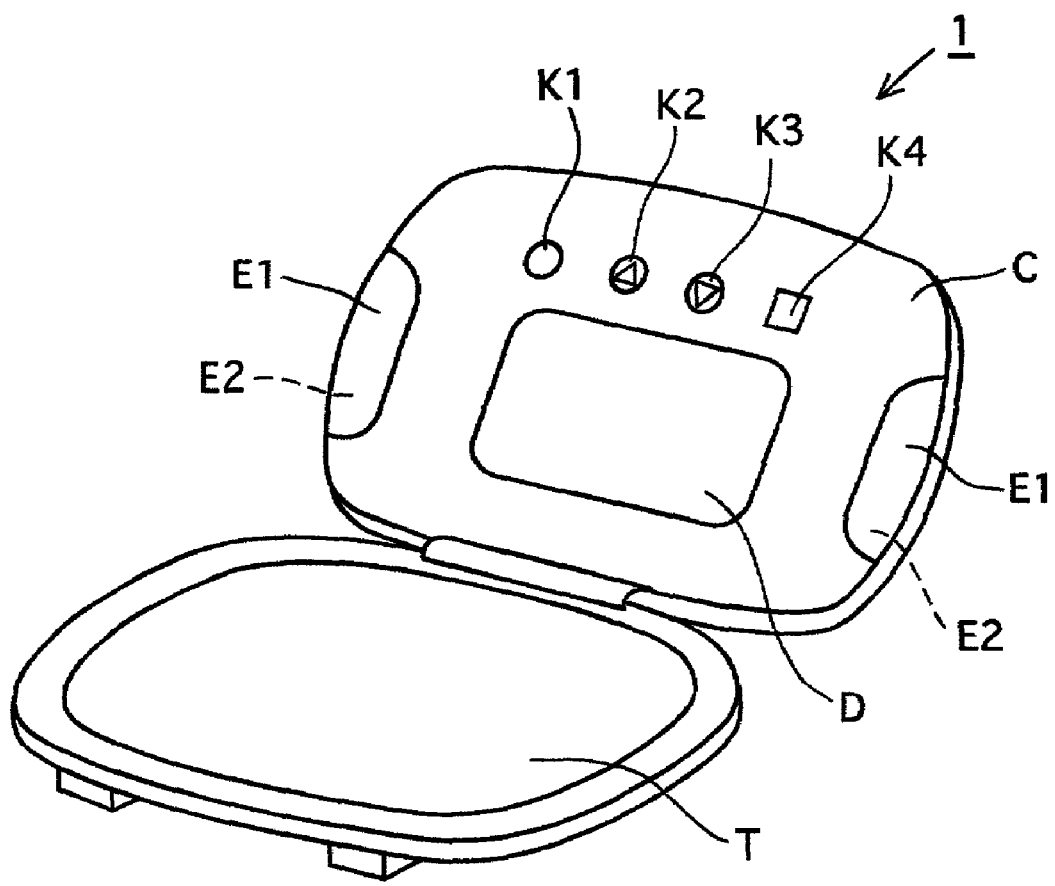
FIG. 1 is a perspective view of an apparatus for managing the quantity of exercising to be healthy according to one embodiment of the present invention.

An apparatus for managing the quantity of exercising to be healthy according to one embodiment of the present invention is described below by referring to accompanying drawings. FIG. 1 illustrates the whole appearance of the exercise managing apparatus 1. As shown, the compact-like casing C has two feeding electrodes E1 and E1 and detecting electrodes E2 and E2 electrically insulated from and fixed to the front and rear sides of the lid of the compact-like casing C, thus forming a four-terminal electrode.

Alternately all the electrodes may be arranged on the front or rear side of the lid.

The lid can be opened or closed to be laid on the casing body T, which is to be fixed to the waist. The lid has an LCD "D", a measurement button K1, a digit ascending button K2, a digit-descending button K3 and a switching button K4 are arranged on the rear side of the lid.

When the measurement button K1 is depressed, the exercising quantity meter or the body fat meter starts a required measurement.

Every time the digit-ascending button K2 has been depressed, the digit ascends one to be inputted.

Likewise, every time the digit-descending button K3 has been depressed, the digit descends one to be inputted.

The switching button K4 is depressed to switch from the exercising quantity measurement to the body fat measurement or inversely, or from the data inputting menu to the target setting menu or inversely.

Personal data of sex, age, height and weight can be inputted by correcting their default values.

Figure 2:
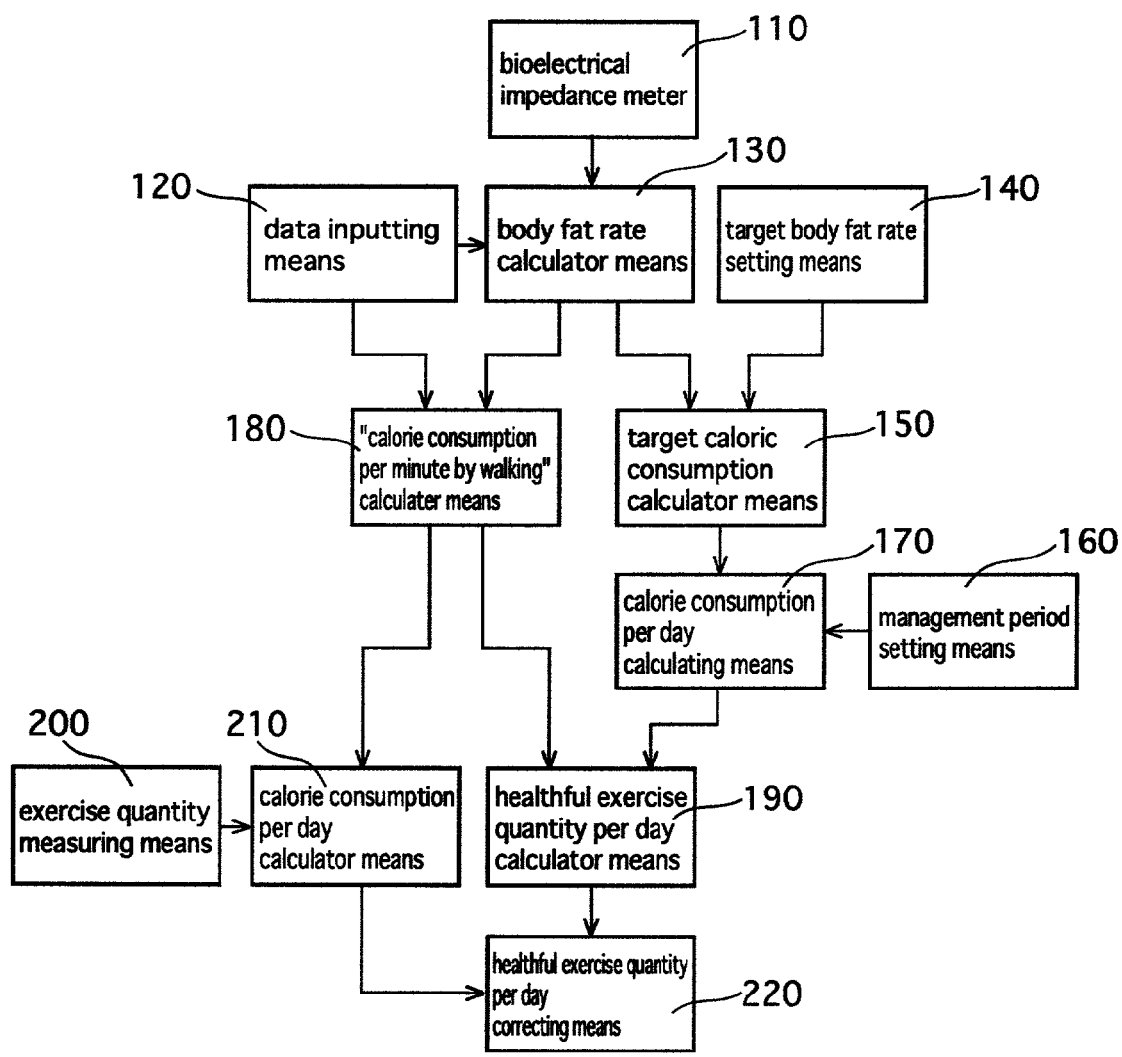
FIG. 2 is a block diagram showing the functions of the exercise managing apparatus according to the present invention.

FIG. 2 shows a block diagram of functions in the exercise managing apparatus.

It includes a bioelectrical impedance meter 110 which can determine the value of bioelectrical impedance appearing between the detecting electrodes E2 and E2, which are applied to a selected part of the living body; data inputting means 120 for inputting the personal data of sex, age, height and weight by using the digit ascending button K2, the digit-descending button K3 and the switching button K4; body fat rate calculator means 130 which can determine the body fat rate on the basis of the personal data and the value of bioelectrical impedance; target body fat rate setting means 140 for setting a desired body fat rate for a target; target caloric consumption calculator means 150 which can determine the calorie consumption required to reach the target body fat rate; management period setting means 160 for determining and setting a length of period long enough to reach the target body fat rate; calorie consumption per day calculating means 170 which can determine the caloric quantity to be consumed each day for the management period; basal metastasis estimating means which can estimate the basal metastasis on the basis both of the personal data and body fat rate; "calorie consumption per minute by walking" calculator means 180 which can determine, in consideration of the individual basal metastasis, the caloric quantity consumed per minute by power-striding or any other exercise taken; healthful exercise quantity per day calculator means 190 which can determine the exercise quantity required to consume the caloric quantity each day to be healthy; exercise quantity measuring means 200; calorie consumption per day calculator means 210 which can determine the caloric quantity consumed per day from the so determined exercise quantity; and healthful exercise quantity per day correcting means 220 responsive to any difference between the previous day's calorie consumption and the target calorie consumption per day for calculating the calorie consumption difference in terms of exercise quantity and for correcting the exercise quantity per day on the basis of the so calculated exercise quantity, the corrected exercise quantity being to be fulfilled on the present day.

Figure 3:
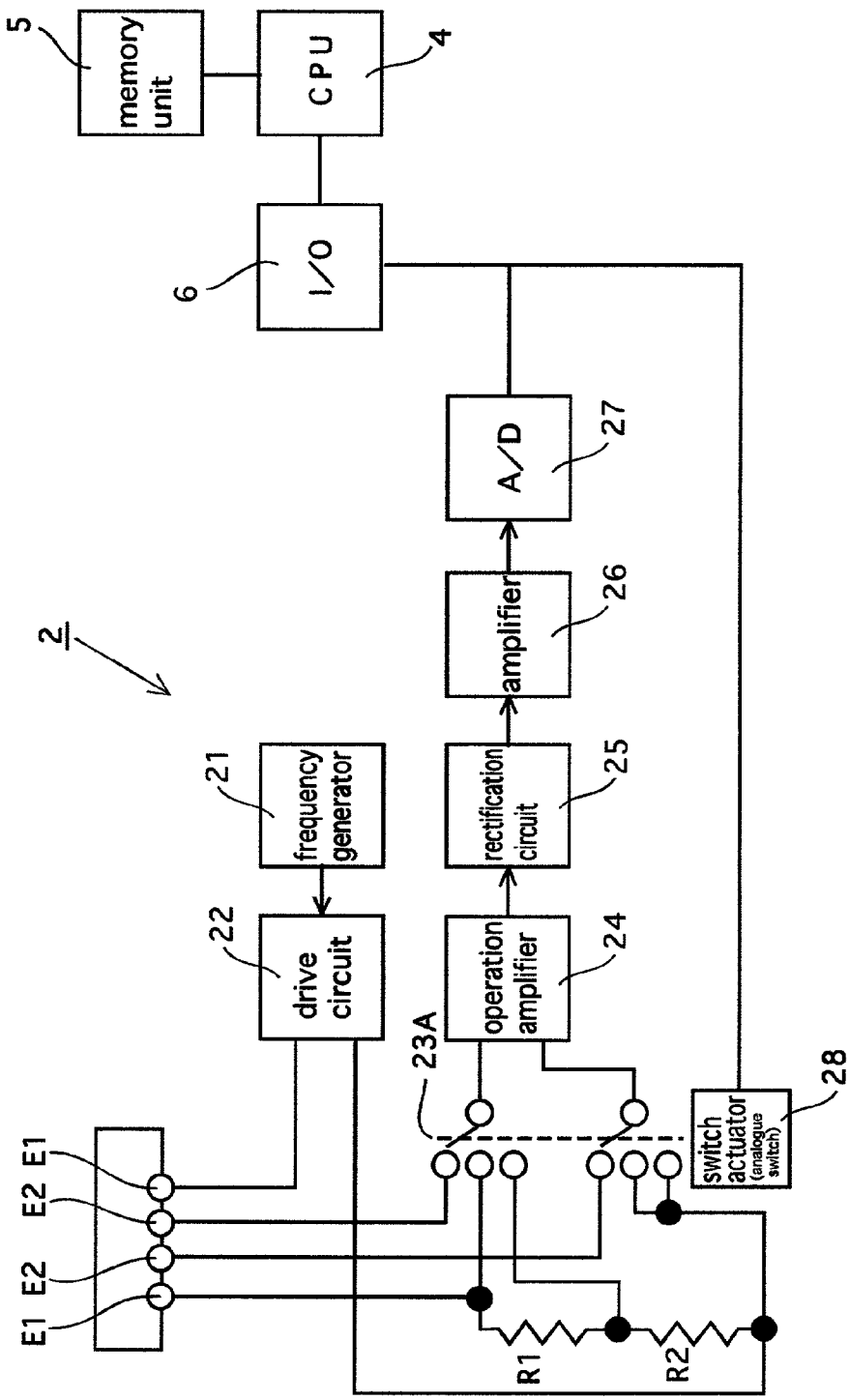
FIG. 3 is a block diagram of a bioelectrical impedance meter installed in the exercise managing apparatus according to the present invention.

Referring to FIG. 3, a bioelectrical impedance measuring circuit 2 comprises: a frequency generator 21 for generating sinusoidal voltage of 50 kHz; a drive circuit 22 connected to the frequency generator 21; a switch 23A for applying the sinusoidal voltage between the opposite feeding electrodes E1 and E1, and hence between both hands, the thumbs and fore-fingers of which are used to pinch the feeding and detecting electrodes E1 and E2 of the lid of the casing C; an operation amplifier 24 to which the voltage appearing between the opposite detecting electrodes E2 and E2 is applied via the switch 23A; a rectification circuit 25 for converting the voltage appearing between the opposite detecting electrodes E2 and E2 to DC voltage; an amplifier 26 for reshaping, level-controlling and off-setting the so converted DC voltage; an analogue-to-digital converter 27; an I/O interface 6, a CPU 4 with an associated memory unit 5 and a switch actuator 28 connected to the interface I/O 6.

To reduce any error in measurement caused by the characteristic variation of parts with time and temperature the bioelectrical impedance measuring circuit is calibrated in terms of its outputting characteristics on the detection side. Specifically, a regression linear equation representing the detected voltage-and-bioelectrical impedance relationship is given by $Z=kV+Co$. The proportional constant k and the fixed constant Co can be determined by applying to the known resistors R1 and R2 the same ac voltage as used in measuring the value of bioelectrical impedance Z and by measuring the voltages V appearing across the resistors R1 and R2.

The switch actuator 28 responds to the control signal sent from the CPU 4 via the I/O 6, so that the contact arm 23A may be thrown on the side on which the resistor R1 (or R2) is connected to the frequency generator 21. Then, the switch actuator 28 responds to the control signal from the CPU 4, so that the contact arm 23B may be thrown on the side on which the resistor R1 (or R2) is connected to the detecting section of the bioelectrical impedance measuring circuit 2.

The target body fat rate setting means 140 permits the user to select a desired body fat rate from the ideal body fat rate menu (ideal fat rate for women ranging from 17 to 24%, and for men ranging from 14 to 20%) and put the so selected body fat rate for the target value.

If no target value should be selected, an appropriate value for men or women is determined automatically in consideration of the measured body fat rate, and the so determined value is set for the target.

The target calorie consumption calculator means 150 determines the body fat quantity to be reduced on the basis of the difference between the target body fat rate and the measured body fat rate, and then the target calorie consumption calculator means 150 calculates the target calorie consumption required to consume the so determined body fat quantity at the calorie-to-fat exchange rate of 7000 kcal to 1 kg:

target calorie consumption (kcal)=(measured body fat rate−target body fat rate)×weight (kg)×7000 (kcal/kg)/100

The management period setting means 160 permits the user to select three months, six months or one year from the management period menu.

If no management period should be selected, an appropriate length of period is automatically selected in consideration of the difference between the measured body fat rate and the target body fat rate.

The so selected length of period is converted to the number of days.

The calorie consumption per day calculating means 170 calculates the caloric quantity to be consumed each day for the management period:

> the healthful caloric quantity to be consumed each day (kcal/day)=the target calorie consumption (kcal)/ the number of days in the management period The exercise calorie consumption per minute calculator means 180 calculates, in consideration of the individual basal metastasis, the caloric quantity consumed per minute by power-striding or any other exercise taken:

> the caloric quantity consumed per minute (kcal/min.) =(the energy-to-metastasis rate×the individual basal metastasis+the rest metastasis) (kcal)/1440 (min.)

The energy-to-metastasis rate can be determined by actual measurements, as for example, follows: it is 3.0 for ordinary walk, 2.0 for moderate walk, 4.7 to 5.5 for brisk walk and 7.0 for jogging. Here, the energy-to-metastasis rate is assumed to be 3.0 for ordinary walk.

The individual basal metastasis can be calculated as follows:

> the basal metastasis=C0×weight×(100−body fat rate)/ 100+C1 where C0 is equal to:
- 24.0349 for women at the age of 40 or less;
- 21.951 for women at the age of 40 or more;
- 27.717 for men at the age of 40 or less; and
- 25.333 for men at the age of 40 or more; and C1 is equal to:
- 427.64 for women at the age of 40 or less;
- 424.38 for women at the age of 40 or more;
- 2188.21 for men at the age of 40 or less; and
- 243.28 for men at the age of 40 or more The rest metastasis is 1.2 times the basal metastasis.

The exercise quantity per day calculator means 190 determines the exercise time per day required to consume the healthful calorie consumption each day, and then it calculates the healthful exercise quantity such as the number of steps in power-striding from the so determined exercise time per day:

> the exercise time per day required to consume the healthful calorie consumption each day (min./ day)=the healthful calorie consumption per day (kcal/day)/the exercise-consumable calorie per min. (kcal/min.)

It should be noted that the minimum length of time taken before the body fat starts burning is 12 minutes long, and that this minimum length of time or longer be added to the required exercise time per day:

> the healthful exercise quantity per day (steps/day)=the required exercise time per day (min./day)×the exercise quantity per minute (steps/min.)

The exercise quantity per minute can be determined by actual measurements, as for example, follows: it is 80 to 100 for ordinary walk, 50 to 80 for moderate walk, 100 to 150 for brisk walk and 150 to 300 for jogging.

Here, it is assumed that the exercise quantity per minute be 80 to 100 for ordinary walk.

The exercise quantity measuring means 200 is a pedometer whose pendulum has a magnetic attached thereto, thereby permitting an associated lead switch to turn on and off while walking. Thus, the steps can be counted in terms of the swinging times of the pendulum.

The pedometer is equipped with an accelerometer, which is responsive to shaky movements for distinguishing ordinary walk, moderate walk, brisk walk and jogging from each other, thus permitting the counting of steps in terms of different walking styles.

One example of the accelerometer uses a strain gauge for detecting the displacement of the weight supported by a spring. It may have a piezoelectric element in place of the spring, which piezoelectric element can measure the acceleration in terms of the electricity, which appears across the element in proportion to the displacement of the weight.

Another example of the accelerometer uses a coil-and-weight in the magnetic field for inducing electromotive force in the coil moving in the magnetic field, thereby measuring acceleration in terms of the induced electromotive force.

The calorie consumption per day calculator means 210 determines the calorie consumption per day by: counting the number of steps for each of the different styles of walking to determine the length of time involved therefor; multiplying the so determined length of time by the calorie consumption per minute; and totaling all the products.

> the length of time per day involved for each of the different styles of walking (min./day)=the number of steps for each style of walking (steps/day)/the number of steps per minute for each style of walking As described above, the number of steps per minute for each style of walking is 80 to 100 for ordinary walk, 50 to 80 for moderate walk, 100 to 150 for brisk walk and 150 to 300 for jogging.

> the calorie consumption per day (kcal/day)=Σ[the length of time per day involved for each style of walking (min./day)×walking calorie per minute for each style of walking (kcal/min.)]

The walking calorie per minute for each style of walking can be obtained from the above equation, which is given by:

> The calorie quantity consumed per minute (kcal/min.) =(the energy-to-metastasis rate×the individual basal metastasis+the metastasis at the rest) (kcal)/ 1440 (min.)

As described earlier, the energy-to-metastasis rate is 3.0 for ordinary walk, 2.0 for moderate walk, 4.7 to 5.5 for brisk walk and 7.0 for jogging.

In a case where the previous day's calorie consumption is above the target calorie consumption per day, the healthful exercise quantity per day correcting means 220 calculates the extra quantity of calorie consumption in terms of exercise quantity such as the number of steps to subtract from the present day's healthful exercise quantity per day.

With the above described structure the user can measure the body fat by using the switch button K4, the digit ascending button K2 and the digit descending button K3, thereby inputting the personal data pertaining to sex, age, height and weight.

If these data remain as they were before, the inputting operation can be omitted.

Next, the electrodes E1 and E2 on the casing C are pinched between selected fingers of both hands, and then the measurement button K1 is depressed to start a required measurement.

After a while the body fat rate is given in the display "D".

In setting a desired body fat rate for the target the switch button K4 is pushed to select the target value among those in the menu while comparing with the measured body fat rate.

If such selection should be omitted, a standard body fat rate is set for the target value.

In measuring the exercise quantity the switch button K4 is pushed to switch to the exercise quantity measuring mode, and then, the measurement button K1 is pushed to start a required measurement.

The actual exercise quantity is shown along with the target value of the healthful exercise quantity per day and the balance to the target value in the display "D".

Every time the body fat rate has been measured, or every time the target value of the body fat rate has been renewed, an initial value is set for the healthful exercise quantity per day. The target value to be fulfilled next day is renewed by adding the remaining quantity or subtracting the extra quantity of exercise produced in the actual exercise quantity of the day.

Figure 4:
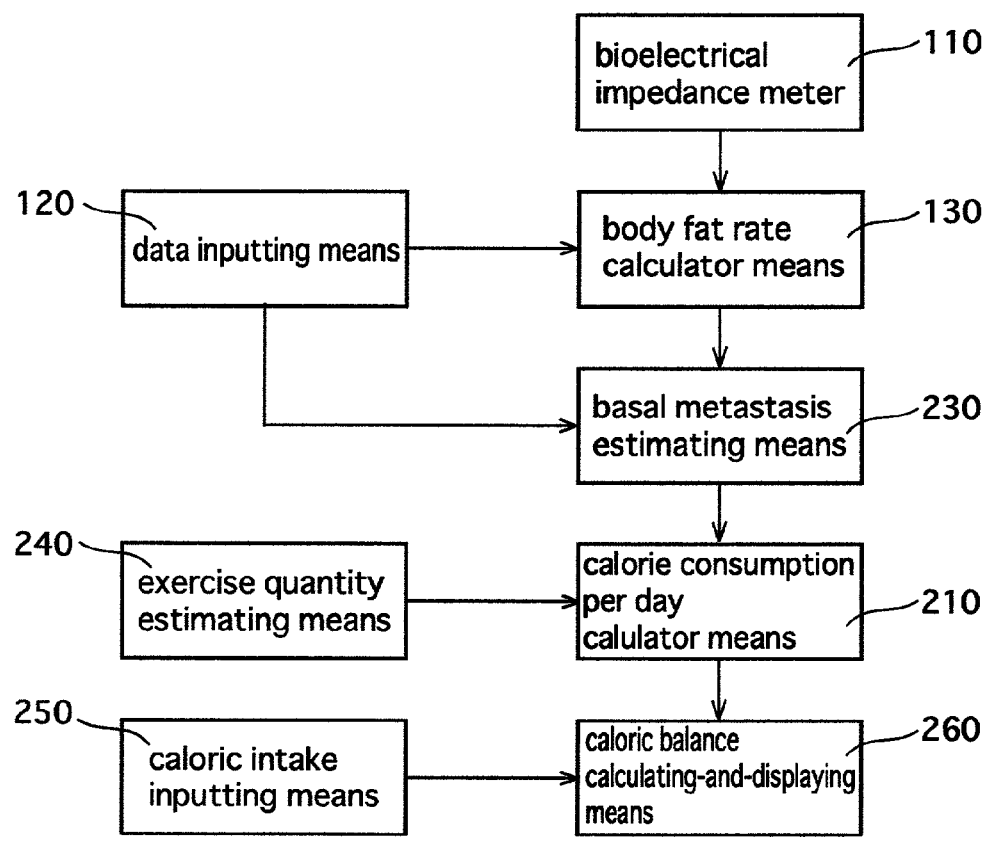
FIG. 4 is a block diagram showing the functions of the exercise managing apparatus according to another embodiment of the present invention.

Referring to FIG. 4, in addition to the bioelectrical impedance measuring means 110, the data inputting means 120, the body fat rate calculating means 130 and the calorie consumption calculator means 210 the exercise managing apparatus may further comprise: basal metastasis estimating means 230 for estimating the basal metastasis on the basis of the personal data and the body fat rate; exercise quantity estimating means 240 for estimating the total exercise quantity from data provided by the exercise quantity measuring means; caloric intake inputting means 250 for inputting the calorie taken in by drinking and taking food; and caloric balance calculating-and-displaying means 260 for determining the difference between the caloric intake per day and the caloric consumption and for showing the balance between the calorie consumption and the caloric intake.

The exercise quantity measuring means 200 is described as a pedometer, but it may be a measuring unit using the accelerometer to determine the standing up-and-sitting down movement and/or the number of moving arms. The so determined movements can be calculated in terms of the number of steps, if such measuring unit is used with the pedometer.

An angle sensor may be used to determine the posture of the user (thereby permitting a decision to be made as to whether he is sitting or standing, whether he is moving his arms, or whether he is swinging his arms for exercise or he is writing), thereby modifying the caloric consumption in terms of the so determined posture.

Such a healthful exercise quantity measuring apparatus may be a card-like or wristwatch-like object, which is convenient to carry.

As may be understood from the above, an apparatus for managing the quantity of exercising to be healthy according to the present invention has exercise quantity measuring means installed therein. It has at least one set of electrodes for use in measuring bioelectrical impedance, data inputting means and a display arranged on its portable casing, and it has body fat rate calculating means installed therein, thus permitting the exercise quantity and the body fat rate to be shown in its display.

The user can realize the result attained by the power-striding or any other exercise in terms of the body fat rate, thereby encouraging the user in his attempt to reduce the fatness, and not allowing him to lose his interest in taking healthful exercise until he has reached the goal.

Also, an apparatus for managing the quantity of exercising to be healthy according to the present invention has exercise quantity measuring means installed therein. It has at least one set of electrodes for use in measuring bioelectrical impedance, data inputting means and a display arranged on its portable casing, and it has body fat rate calculating means, target body fat rate setting means and healthful exercise quantity setting means for setting the healthful exercise quantity required to attain the target body fat rate, so that the exercise quantity such as the number of steps, the body fat rate and the health exercise quantity may be shown in its display.

Not only the exercise quantity is measured and shown, but also the target exercise quantity enough to reduce fatness and become healthy is shown, and therefore, the user can have a confidence in reaching the goal someday.

What is claimed is:

1. An apparatus for managing the quantity of exercising to be healthy, comprising:

a portable casing with a display fixed thereon, said portable casing having exercise quantity measuring means installed therein;

at least one set of electrodes fixed to the surface of said portable casing for measuring bioelectrical impedance;

data inputting means for inputting personal data including sex, age, height and weight;

and body fat rate calculating means for determining the body fat rate on the basis of said personal data and the value of said bioelectrical impedance, which bioelectrical impedance appears between two selected electrodes when a controlled weak current flows between the two selected electrodes through a living body, whereby the exercise quantity along with the body fat rate are shown in said display.

2. The apparatus for managing the quantity of exercising to be healthy according to claim 1, further comprising:

basal metastasis estimating means for estimating the basal metastasis on the basis of said personal data and said body fat rate;

exercise quantity estimating means for estimating the total exercise quantity on the basis of data provided by means of said exercise quantity measuring means;

calorie consumption calculating means for determining the calorie consumption on the basis of the estimated basal metastasis and the total exercise quantity;

caloric intake inputting means for inputting the calorie taken in by drinking and taking food; and caloric balance calculating-and-displaying means for determining the difference between the caloric intake per day and the calorie consumption and for displaying the balance between the caloric intake and the calorie consumption.

3. An apparatus for managing the quantity of exercising to be healthy, comprising:

a portable casing with a display fixed thereon, said portable casing having exercise quantity measuring means installed therein;

at least one set of electrodes fixed to the surface of said portable casing for measuring bioelectrical impedance;

data inputting means for inputting personal data including sex, age, height and weight;

body fat rate calculating means for determining the body fat rate on the basis of said personal data and the value of said bioelectrical impedance, which bioelectrical impedance appears between two selected electrodes when a controlled weak current flows between the two selected electrodes through a living body;

body fat rate setting means for setting a desired body fat rate as a target; and healthful exercising quantity setting means for determining the quantity of exercising each day toward the desired body fat rate on the basis of the so determined body fat rate and for setting the so determined quantity of exercise per day, whereby the exercise quantity along with the body fat rate and the healthful exercising quantity per day are shown in said display.

4. The apparatus for managing the quantity of exercising to be healthy according to claim 3, further comprising:

healthful exercising quantity renewing means for renewing the healthful exercising quantity per day in consideration of the exercising quantity determined the day before, the required renewal being made every day.

* * * * *